United States Patent [19]

Lunn

[11] Patent Number: 5,755,704
[45] Date of Patent: May 26, 1998

[54] THINWALL GUIDE CATHETER

[75] Inventor: Peter A. Lunn, Beverly, Mass.

[73] Assignee: Medtronic, Inc., Minneapolis, Minn.

[21] Appl. No.: 739,337

[22] Filed: Oct. 29, 1996

[51] Int. Cl.⁶ ............................................... A61M 25/00
[52] U.S. Cl. ............................................... 604/282; 128/658
[58] Field of Search ............................... 604/282, 281, 604/280, 264, 95; 128/656–658

[56] References Cited

U.S. PATENT DOCUMENTS

| | | | |
|---|---|---|---|
| 4,516,972 | 5/1985 | Samson | 604/282 |
| 4,636,346 | 1/1987 | Gold et al. | 264/139 |
| 4,764,324 | 8/1988 | Burnham | 264/103 |
| 4,817,613 | 4/1989 | Jaraczewski et al. | 128/658 |
| 4,863,442 | 9/1989 | DeMello et al. | 604/282 |
| 4,899,787 | 2/1990 | Ouchi et al. | 138/131 |
| 5,019,057 | 5/1991 | Truckai | 604/282 |
| 5,176,660 | 1/1993 | Truckai | 604/282 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |
| 5,279,596 | 1/1994 | Castaneda et al. | 604/282 |
| 5,334,169 | 8/1994 | Brown et al. | 604/282 |
| 5,403,292 | 4/1995 | Ju | 604/282 |
| 5,423,773 | 6/1995 | Jiminez | 604/282 |
| 5,545,149 | 8/1996 | Brin et al. | 604/265 |

Primary Examiner—John D. Yasko
Attorney, Agent, or Firm—David S. Brin; Dianne M.F. Plunkett; Harold R. Patton

[57] ABSTRACT

An apparatus and method of making a thinwall guide catheter useful in delivery of therapeutic devices through a body vessel. The method comprises braiding a flat wire over the surface of a cylindrical core, placing a heat bondable polymer tube over the braid, surrounding the polymer tube with a heat shrink sleeve, heating the assembly to a temperature and for a time period sufficient to expand the core into braid interstices and bond the polymer tube to substantially only the outer surface of the braid and finally removing the heat shrink sleeve and core. The resulting guide catheter has approximately half the wall thickness of prior guide catheters and has excellent column stiffness and kink resistance.

14 Claims, 4 Drawing Sheets

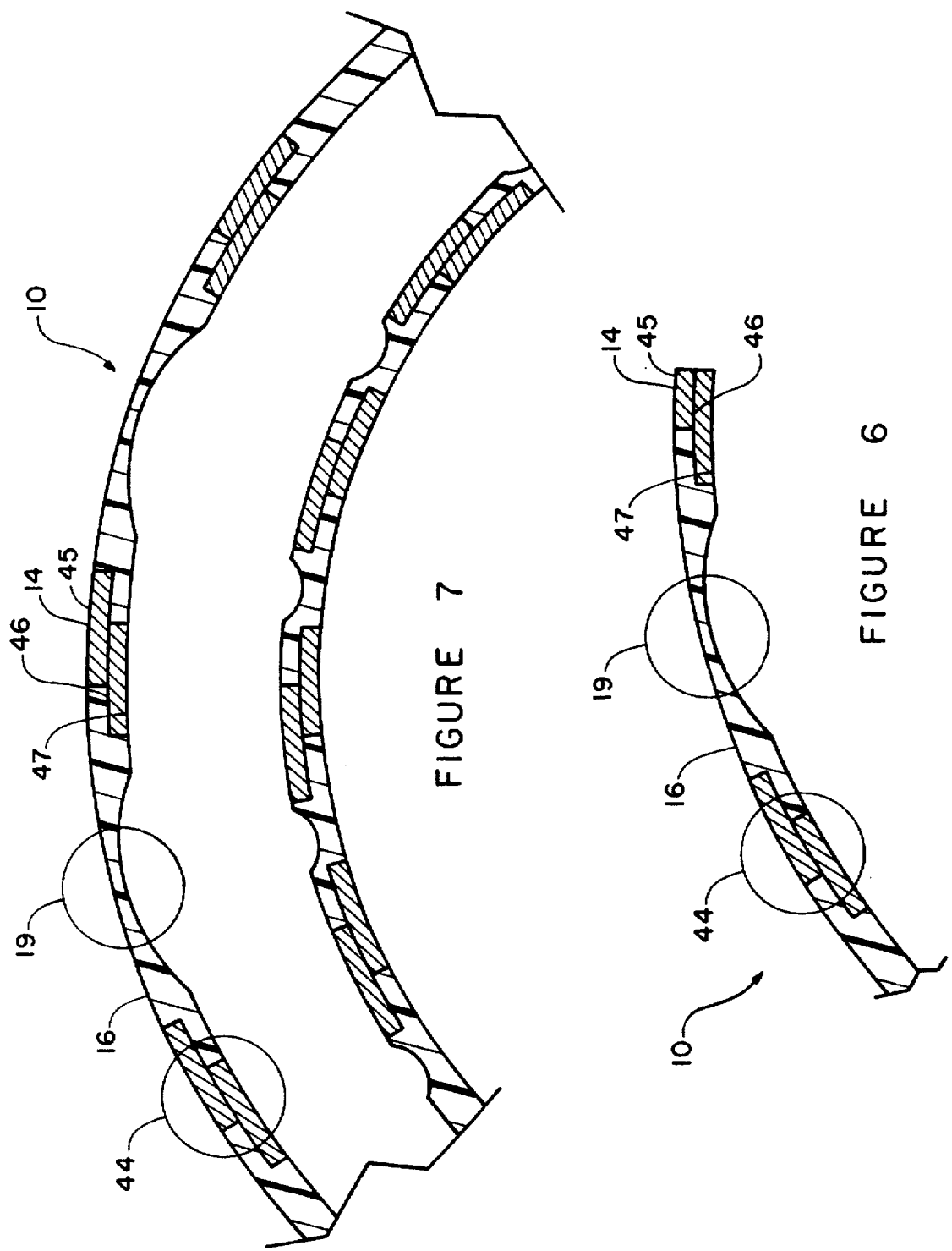

THINWALL GUIDE CATHETER

FIELD OF THE INVENTION

This invention relates to a thinwall guide catheter for insertion into body vessels to deliver a therapeutic device to a selected site and, more specifically, to an improved guide catheter and method of making, the guide catheter having a thinner wall and excellent stiffness, kink resistance and torque transfer characteristics.

BACKGROUND OF THE INVENTION

Present guide catheters generally are formed as a three layer composite tube. A liner is utilized to provide a lubricious surface to aid in device passage through the lumen of the guide. The next layer is a braid material, typically a stainless steel round wire braid, which is positioned directly over the liner. An outer jacket encapsulates the braid and is bonded to the liner through braid interstices to create a monolithic structure from the three components. Typically a liner made in this manner is about 0.002 in. thick, the braid is 0.002 in. thick (0.004 at the crossovers) and the outer jacket thickness is dictated by the outside diameter of the catheter. Typical overall guide catheter wall thicknesses are about 0.010 in., providing a 0.086 in. diameter lumen on an about 0.106 in. catheter. Thinner guide catheter walls are desirable to provide maximum lumen diameter for passage of therapeutic devices.

Guide catheters are typically used in procedures such as percutaneous transluminal coronary angioplasty (PTCA) which are intended to reduce arterial build-up of cholesterol fats or atherosclerotic plaque. Typically a guidewire is steered through the vascular system to the site of therapy. A guiding catheter can then be advanced over the guidewire and finally a balloon catheter advanced within the guiding catheter over the guidewire. A thin wall on the guide catheter will permit passage of a balloon having greater diameter, as is often necessary or desirable.

A number of different catheters have been developed that use braided or coiled reinforcing strands embedded in a plastic wall. Typical of these are the catheter structures described by Truckai in U.S. Pat. No. 5,176,660, Samson in U.S. Pat. No. 4,516,972 and Jaraczewski in U.S. Pat. No. 4,817,613. While providing acceptable torque and column strength, these arrangements tend to show low kink resistance and have undesirably thick walls.

Thus, there is a continuing need for improvements in guide catheters having reduced wall thicknesses with resulting increased lumen diameters while providing improved stiffness and torque transfer characteristics and high kink resistance.

SUMMARY OF THE INVENTION

The above noted problems are overcome by an apparatus and method of making guide catheters which, comprises the steps of providing a disposable core, braiding a flat metal wire over the core, pressing a heat bondable polymer tube over the braid and heating the assembly for sufficient time to bond the tube only to the outer surface of the braid.

A guide catheter made according to the method of this invention can have a wall thickness of about 0.005 inch, approximately half of the thickness required in conventional catheters to produce comparable physical characteristics including kink resistance and column strength.

Any suitable core material may be used. The core material should have sufficient strength to resist pressure during the heat bonding step, should not bond to the heat bonding polymer and should have low friction with the braid for easy removal. A solid fluorocarbon polymer is preferred for the core. While in some cases the core can be simply slid out of the braided tube, in some cases it is preferred that ends of the core extending beyond the braided tube be grasped and pulled apart slightly to stretch the core and reduce the cross section of the core to aid in sliding the core from the tube.

Wire may be braided in any suitable manner to form the braided tube. The braid is formed from a stiff flat wire, preferably a stiff metal having a width from about 0.005 to 0.015 inch and a thickness of from about 0.0007 to 0.0010 inch.

A heat shrink sleeve is used to perform the heat bonding. The heat shrink sleeve can be formed from any suitable material in a conventional manner. Typical heat shrink materials include fluorinated ethylene-propylene, tetrafluoroethylene and polyesters. Of these, an optimum combination of shrink pressure and shrinking temperature is found with fluorinated ethylene-propylene.

Preferably, a lubricant is coated onto the internal guide catheter surface to allow a balloon catheter or other device to be inserted into the guide catheter to be inserted and removed using less force.

It is, therefore, an object of this invention to provide an improved thinwall guide catheter with improved physical characteristics. Another object is to provide a thinwall guide catheter including a flat wire braid wherein the braid density or "pic count" is dynamically variable in response to bending, axial, or torsional loads. Another object is to make a thinwall guide catheter wherein the jacket is of variable thickness to permit dynamic expansion or contraction in response to bending, axial, or torsional loads. Another object is to make a thinwall guide catheter having improved kink resistance and column stiffness. Yet another object is to produce a thinwall guide catheter capable of bending to a smaller radius in a body lumen than conventional catheters while avoiding kinking.

BRIEF DESCRIPTION OF THE DRAWINGS

Details of the invention, and of preferred embodiments thereof, will be further understood upon reference to the drawing, wherein:

FIG. 6, is a portion of FIG. 4 with the core removed from the catheter; and

FIG. 7 is a view of FIG. 2 in a bent configuration such that the pic count is greater on the inside of the bending radius than on the outside of the bending radius.

DETAILED DESCRIPTION OF PREFERRED EMBODIMENTS

Figure 1:
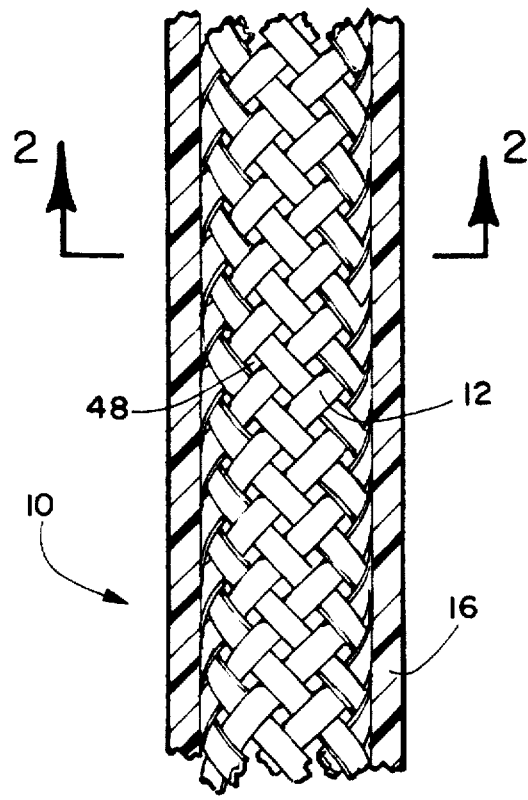
FIG. 1 is an axial section view through a thinwall guide catheter of this invention.
Figure 2:
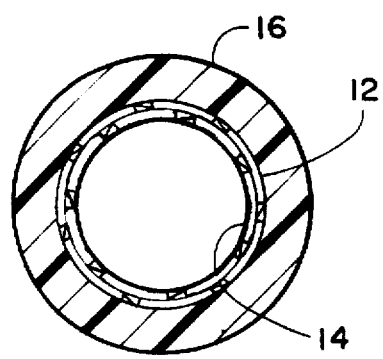
FIG. 2 is a transverse section view, taken on line 2—2 in FIG. 1.

Referring to FIGS. 1 and 2, there is seen axial and transverse section views, respectively, through a thinwall guide catheter 10 made in accordance with this invention. A braided tube 12 of wires 14 is bonded within a polymer tube jacket 16. While a fairly loose braid density is shown for clarity, a tight braid density is often preferred. Jacket 16 is bonded to the outer surfaces of braided tube 12, with little material in the interstices 48 between adjacent wires 14 and essentially no polymer overlapping the inside surface of the braided tube 12.

The cross section of wires 14 may be generally rectangular, preferably with rounded edges. Alternatively, the cross section may be generally oval or elliptical, if desired. An optimum flat wire material is fully tempered 304 stainless steel. The selected wire is braided in a conventional manner over the core. Any suitable braid configuration, in particular any suitable pic count may be used. A braided tube 12 with from about 45 to about 55 cross-overs per inch is preferred. About 50 cross-overs per inch being the most optimum. Wires 14 define a "one (wire) under-one (wire) over" braiding pattern so that the wires 14 form an interlocking mesh with each other. For best results, the wires 14 have thicknesses of from about 0.0007 to 0.0010 inch and widths of from about 0.010 to 0.015 inch. Optimum results are achieved with a 0.0007 in. thick braid producing a 0.0014 in. thickness at the crossovers.

Any suitable polymer that will bond to wires 14 when heated to a suitable temperature may be used for the jacket 16. Typical such polymers include polyether block amides, polyurethanes, polyethylene. Polyamides and mixtures thereof. Of these, optimum results are obtained with the PEBAX® brand polyether block amide available from the Elf Atochem Corporation. Philadelphia, Pa. Using a jacket 16 having an average thickness of about 0.0036 inch, overall wall thicknesses of about 0.005 inch are achieved. A reduction of wall thickness from previous catheters is thus about 50%. This provides an 0.084 inch lumen in a 7 French (0.094 inch) catheter.

Figure 4:
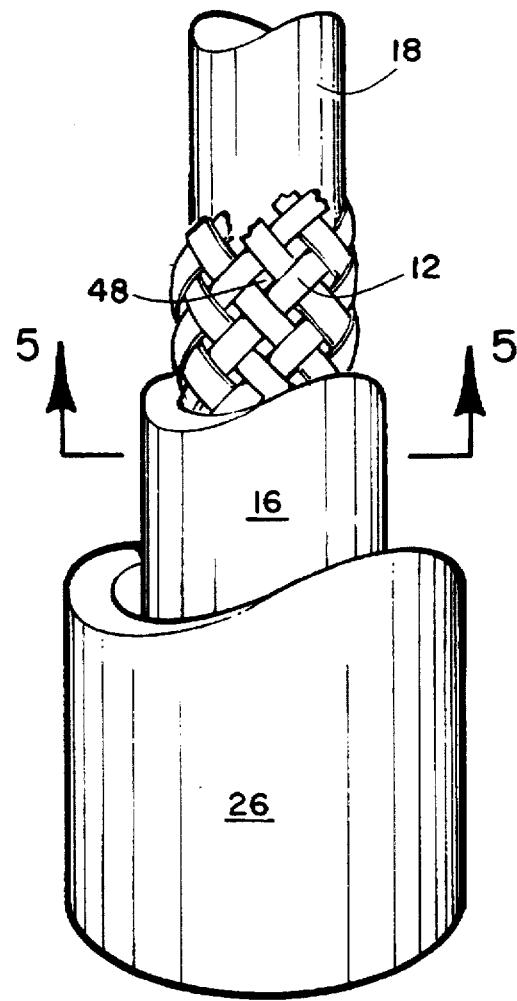
FIG. 4 is a perspective view of a newly completed thinwall guide catheter upon completion of manufacture and prior to removal of shaping components, with portions cut away.
Figure 3:
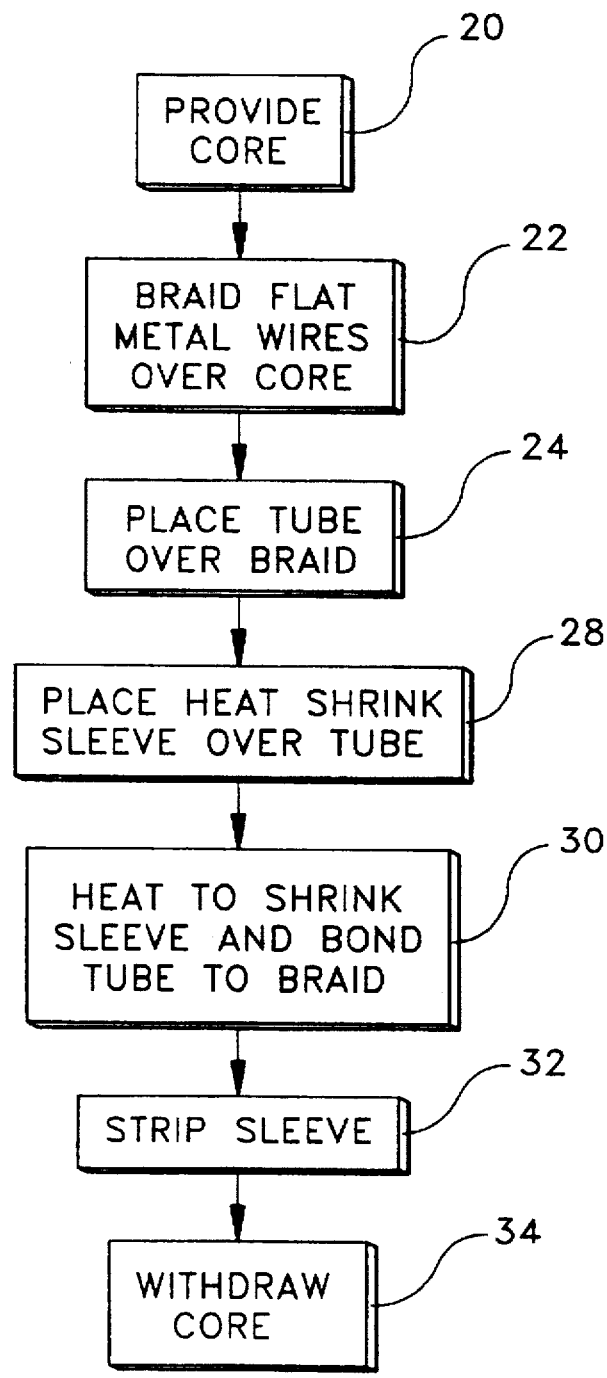
FIG. 3 is a flow chart illustrating the steps in the guide catheter manufacturing method of this invention.

FIG. 3 is a flow diagram illustrating the steps in the manufacture of the improved thinwall guide catheter of this invention. FIG. 4 shows a perspective view, partly cut away, of the assembly for manufacturing the improved catheter.

A core 18 is provided, as indicated in step 20, around which the flat wire 14 can be braided as indicated in step 22. Any suitable core material that will withstand the processing conditions and can be easily removed from the product tube may be used. The material of core 18, however, should be softer than that of the jacket 16 so that the core material will expand into the interstices 48 of the braided tube 12 under the temperatures and pressures of the heat bonding process to essentially the outer surface of the braided tube 12. Typical core materials include fluorocarbon resins, such as tetrafluoroethylene and fluorinated ethylene-propylene resins. Of these, best results are obtained with tetrafluoroethylene, available under the Teflon® trademark from the E.I. duPont de Nemours & Co.

The jacket 16, in the form of a tube, is then placed over braided tube 12 on core 18, as indicated in step 24. A length of heat shrink sleeve 26, in the form of a tube, is then placed over the jacket 16, as indicated in step 28. Heat shrink sleeve 26 should be selected in material and thickness to provide the optimum pressure at an optimum temperature. Best results are obtained with fluorinated ethylene-propylene resins of the sort available from the E.I. duPont de Nemours & Co.

The resulting assembly is heated to shrink the heat shrink sleeve 26 and bond the jacket 16 to the braided tube 12, as indicated in step 30. Any suitable time, temperature and heating method may be used. Insufficient time and/or a lower than necessary temperature will result in a poor bond between jacket 16 and braided tube 12 and undesirably low stiffness values. Excessive time and/or excessively high temperatures will result in substantial encapsulation of the braided tube 12 by the jacket 16. This produces a great reduction in angular deflection to kink.

Through the proper selection of core material and processing conditions, the jacket 16 will be bonded only to the outer surface of the braided tube 12. Optimum processing conditions for a particular material for the jacket 16 can be easily obtained by making a series of catheters using different combinations of heating time and temperature. The catheters can be examined to determine the combination of time and temperature that produces catheters having the desired bonding to only the outer surface of the braided tube 12. which results in an optimum combination of column strength and kink resistance for an intended catheter end use.

Upon completion of the heating step, generally with cooling to room temperature, heat shrink sleeve 26 is stripped away as indicated by step 32 and core 18 is withdrawn as shown in step 34. Preferably, core 18 is slightly stretched to slightly reduce core cross section and ease removal. Preferably, after the core 18 is removed, a lubricant such as a silicone lubricant, is coated over the inside surface of braided tube 12 to facilitate device movement within the catheter 10.

Figure 5:
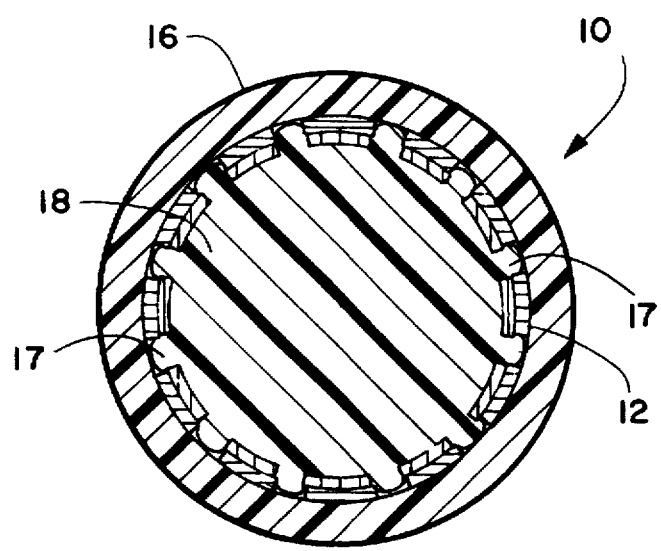
FIG. 5 is a section view taken on line 5—5 in FIG. 4 with the core in an expanded state.

FIG. 5 is a section through the assembly of FIG. 4, taken on line 5—5 during the heating step. This section passes through the cross-over points of the individual wires 14 of the braided tube 12. As seen, core 18 has expanded into the interstices 48 of the braided tube 12 so that the material of jacket 16 cannot penetrate into them. The "bulges" 17 in the core 18 at the interstices 48 of the braided tube 12 will retract when core 18 is cooled and can be further loosened when the ends of the core 18 are moved apart to stretch and reduce the cross-section of the core 18. Preferably, the ends of the core 18 are pulled away from each other to stretch the core 18 and reduce core diameter to allow easy withdrawal of the core 18 from the completed catheter 10.

Referring to FIG. 6, which is a section through the assembly of FIG. 4 with the core 18 of FIG. 5 removed from the catheter 10. The bulges 17 in the core 18 of FIG. 5 produce voids 19 in the jacket 16 at each interstitial location 48 between preferably four (4) adjacent cross-over points 44 of braided tube 12. The cross-over points, 44, define an outer surface 45, an inner surface 46, and an intermediate surface 47. The voids 19 in the jacket 16 are generally hemispherical in shape, producing corresponding variable thicknesses of the jacket 16 between the cross-over points 44 of the braided tube 12. The jacket 16 varies in thickness from a minimum in the center of the four respective cross-over points 44 of the braided tube 12 to a maximum at the junctions of the jacket 16 with the outer surface 45 of the respective cross-over points 44 of the braided tube 12. The effect of the voids 19 in the jacket 16 is that when the catheter 10 is subjected to bending, axial, or torsional loading, the jacket 16 is permitted to dynamically expand and contract within the interstices 48 of the braided tube 12 in response to the loads and thus resist a buckling failure.

With jacket 16 bonded only to the outer surface of braided tube 12, and the wires 14 forming a "one under-one over" braiding pattern as described above, the wires 14 are preferably bonded to the jacket 16 at every other cross-over point 44, with the cross-over points 44 therebetween being free from a bond with jacket 16. As a result of this preferred bonding geometry, when a region along the catheter is bent, the segments of individual wires 14 which are between adjacent points of bonding with the jacket 16 can move in response bending, axial, or torsional loading. For example, as seen in FIG. 7 segments of wire 14 are permitted to move toward each other on the inside of a bending radius and move apart at the outside of the bending radius, providing a resistance to kinking of the catheter 10. The effect of the wires 14 moving relative to each other in response to bending or torsion of the catheter results in a dynamically variable pic count in the catheter. This ability to vary the pic count at bends is of great importance in avoiding catheter kinking in use. Thus, the two-fold effect of a jacket 16 which is permitted to dynamically expand and contract within the interstices 48 of the braided tube with a dynamically variable pic count results in superior performance in the thinwall guide catheter.

With jacket 16 bonded only to the outer surface 45 of the cross-over points 44 of the braided tube 12, and the wires 14 forming a "one under-one over" braiding pattern as described above, the individual wires 14 are preferably bonded to the jacket 16 at every other cross-over point at the outer surfaces 45. The jacket 16, however, is neither bonded to the inner surface 46, nor bonded to the intermediate surface 47 of the cross-over points 44 at the outer surface, with the cross-over points therebetween being free from a bond with jacket 16. As a result of this preferred bonding geometry, when a region along the catheter is bent, the segments of individual wires 14 which are between adjacent points of bonding with the jacket 16 can move in response bending, axial, or torsional loading. For example, segments of wire 14 are permitted to move toward each other on the inside of a bending radius and move apart at the outside of the bending radius, providing a resistance to kinking of the catheter 10. The effect of the wires 14 moving relative to each other in response to bending or torsion of the catheter results in a dynamically variable pic count in the catheter. This ability to vary the pic count at bends is of great importance in avoiding catheter kinking in use.

The following examples provide further preferred embodiments of the catheter manufacturing method of this invention. Parts and percentages are by weight unless otherwise indicated.

EXAMPLE I

A catheter was prepared as follows. A core of tetrafluoroethylene from the duPont company, having a circular cross section and a diameter of about 0.084 inch, was provided. The core was braided in a Model K80/16-1K -72 braiding machine from the Steeger company with No. 304 flat stainless steel wire having a width of about 0.010 inch and thickness of about 0.0007 inch in a pattern producing a pic count of about 50 cross-overs per inch. A tube of polyethylene block amide polymer, available from Atochem, Inc. under the PEBAX® 7033(70D) designation was placed over the braided core. The tube has an inside diameter of about 0.087 inch and a wall thickness of about 0.004 inch. A fluorinated ethylene-propylene sleeve, available from Zeus, Inc. under the FEP heat shrink tubing designation and having an inside diameter of about 0.117 inch was slipped over the PEBAX® tube. The resulting assembly was placed in a 250° C. oven for about 5 minutes, then removed and allowed to cool to room temperature. The shrink tube was removed and the core withdrawn. The resulting tube has the outer jacket bonded to only the outside surface of the braid. The resulting catheter has approximately a 40 degree improvement in angular deflection to kink when compared to similar catheters having the braid encapsulated in the polymer and has excellent column strength. Repeated bending of the tube does not significantly lower the stiffness values.

EXAMPLES II–V

The manufacturing process of Example I is repeated four times, with the following differences:

Example II: Oven temperature 180° C., heating time 5 minutes,

Example III: Oven temperature 180° C., heating time 10 minutes,

Example IV: Oven temperature 250° C., heating time 7 minutes, and

Example V: Oven temperature 300° C., heating time 5 minutes.

The catheter produced in Example II has good kink resistance but low column strength. That made in Examples II and III have good kink resistance. In Examples IV and V, the polymer tube material penetrates into the interstices 48 of the braided tube and at least partially encapsulates the braid. Kink resistance is much lower than in Example I, although column strength is good.

EXAMPLE VII

An animal study was conducted, with a 35 kilogram canine with femoral cut down and using a 9F percutaneous sheath. Attempts to emplace a standard Sherpa® guide catheter was unsuccessful due to the relatively small canine anatomy. A guide catheter as described in Example I was successfully intubated into the left coronary artery. This guide catheter was found to be easier to turn and more responsive to movement.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

What is claimed is:

1. A thinwall guide catheter, comprising:

an elongated braided tube, the braided tube having an outer diameter and an inner diameter, the braided tube having a plurality of elongated wires, one of each of the elongated wires being meshed with an other of each of the elongated wires, one of each of the elongated wires defining with the other of each of the elongated wires a plurality of cross-over points, one of each of the cross-over points having an outer surface, an inner surface, and an intermediate surface, one of each of the cross-over points defining a plurality of interstices, one of each of four adjacent cross-over points defining one of each of the interstices therebetween;

an elongated jacket, the elongated jacket having an inner diameter and an outer diameter, the inner diameter of the elongated jacket being disposed over the outer diameter of the braided tube, the elongated jacket being bonded to one of each of the outer surface of the cross-over points, the elongated jacket being unbonded to one of each of the intermediate surface of the cross-over points, the elongated jacket being unbonded to one of each of the inner surface of the cross-over points;

so that, in response to bending, axial, or torsional loads impressed on the catheter, one of each of the inner and intermediate surfaces of the cross-over points permit one of each of the elongated wires to expand and contract relative to another of each of the elongated wires.

2. The thinwall guide catheter according to claim 1 wherein the braided tube and the elongated jacket have a combined thickness of from about 0.004 to 0.005 inch.

3. The thinwall guide catheter according to claim 1 wherein the elongated wires have a width of from about 0.005 to 0.015 inch and a thickness of from about 0.0007 to 0.0010 inch and the width lies generally parallel to the outer diameter of the braided tube.

4. The thinwall guide catheter according to claim 1 wherein the elongated jacket is formed from a polymer selected from the group consisting of polyether block amides, polyurethanes, polyethylene, polyamides and mixtures thereof.

5. The thinwall guide catheter according to claim 1 wherein the elongated wires are formed from 304 fully tempered stainless steel.

6. The thinwall guide catheter according to claim 1 wherein the braided tube has a predetermined pic count along regions of the catheter when straight, a higher pic count along the inside of regions when bent and a lower pic count along the outside surface of regions when bent.

7. A thinwall guide catheter, comprising:

an elongated braided tube, the braided tube having an outer diameter and an inner diameter, the braided tube having a plurality of elongated wires, one of each of the elongated wires being meshed with an other of each of the elongated wires, one of each of the elongated wires defining with the other of each of the elongated wires a plurality of cross-over points, one of each of the cross-over points having an outer surface, an inner surface, and an intermediate surface, one of each of the cross-over points defining a plurality of interstices, one of each of four adjacent cross-over points defining one of each of the interstices therebetween;

an elongated jacket, the elongated jacket having an inner diameter and an outer diameter, the inner diameter of the elongated jacket being disposed over the outer diameter of the braided tube, the elongated jacket being bonded to one of each of the outer surface of the cross-over points, the elongated jacket being unbonded to one of each of the intermediate surface of the cross-over points, the elongated jacket being unbonded to one of each of the inner surface of the cross-over points, the elongated jacket having a first thickness where the elongated jacket is bonded to one of each of the outer surface of the cross-over points, the elongated jacket having a varying thickness over one of each of the interstices, the elongated jacket having a minimum thickness over the center of one of each of the interstices;

so that, in response to bending, axial, or torsional loads impressed on the catheter, one of each of the inner and intermediate surfaces of the cross-over points permit one of each of the elongated wires to expand and contract relative to another of each of the elongated wires and the elongated jacket is permitted to expand and contract over the interstices.

8. The thinwall guide catheter according to claim 7 wherein the braided tube and the elongated jacket have a combined thickness of from about 0.004 to 0.005 inch.

9. The thinwall guide catheter according to claim 7 wherein the elongated wires have a width of from about 0.005 to 0.015 inch and a thickness of from about 0.0007 to 0.0010 inch and the width lies generally parallel to the outer diameter of the braided tube.

10. The thinwall guide catheter according to claim 7 wherein the elongated jacket is formed from a polymer selected from the group consisting of polyether block amides, polyurethanes, polyethylene, polyamides and mixtures thereof.

11. The thinwall guide catheter according to claim 7 wherein the elongated wires are formed from 304 fully tempered stainless steel.

12. The thinwall guide catheter according to claim 7 wherein the braided tube has a predetermined pic count along regions of the catheter when straight, a higher pic count along the inside of regions when bent and a lower pic count along the outside surface of regions when bent.

13. The thinwall guide catheter according to claim 7 wherein the elongated jacket defines a generally hemispherical shape over one of each of the interstices.

14. A thinwall guide catheter, comprising:

an elongated braided tube, the braided tube having an outer diameter and an inner diameter, the braided tube having a plurality of elongated wires, the braided tube having a predetermined pic count along regions of the catheter when straight, one of each of the elongated wires having a width of from about 0.005 to 0.015 inch and a thickness of from about 0.0007 to 0.0010 inch and the width lies generally parallel to the outer diameter of the braided tube, one of each of the elongated wires being formed from 304 fully tempered stainless steel, one of each of the elongated wires being meshed with an other of each of the elongated wires, one of each of the elongated wires defining with the other of each of the elongated wires a plurality of cross-over points, one of each of the cross-over points having an outer surface, an inner surface, and an intermediate surface, one of each of the cross-over points defining a plurality of interstices, one of each of four adjacent cross-over points defining one of each of the interstices therebetween;

an elongated jacket, the elongated jacket having an inner diameter and an outer diameter, the elongated jacket is formed from a polymer selected from the group consisting of polyether block amides, polyurethanes, polyethylene, polyamides and mixtures thereof, the inner diameter of the elongated jacket being disposed over the outer diameter of the braided tube, the elongated jacket being bonded to one of each of the outer surface of the cross-over points, the elongated jacket being unbonded to one of each of the intermediate surface of the cross-over points, the elongated jacket being unbonded to one of each of the inner surface of the cross-over points, the elongated jacket having a first thickness where the elongated jacket is bonded to one of each of the outer surface of the cross-over points, the elongated jacket having a varying thickness over one of each of the interstices, the elongated jacket having a minimum thickness over the center of one of each of the interstices, the elongated jacket defining a generally hemispherical shape over one of each of the interstices;

so that, the braided tube and the elongated jacket have a combined thickness of from about 0.004 to 0.005 inch, and that, in response to bending, axial, or torsional loads impressed on the catheter, one of each of the inner and intermediate surfaces of the cross-over points permit one of each of the elongated wires to expand and contract relative to another of each of the elongated wires resulting in a higher pic count along the inside of regions when bent and a lower pic count along the outside surface of regions when bent and the elongated jacket is permitted to expand and contract over the interstices.

* * * * *